United States Patent [19]

Nöller

[11] 4,209,586
[45] Jun. 24, 1980

[54] METHOD OF TESTING THE EFFECTIVENESS OF A GROWTH INHIBITING AGENT ON A MICROORGANISM

[76] Inventor: Hans G. Nöller, 1512 Basswood Cir., Glenview, Ill. 60025

[21] Appl. No.: 815,658

[22] Filed: Jul. 14, 1977

[51] Int. Cl.² ............................ C12Q 1/18; C12M 1/34
[52] U.S. Cl. ...................................... 435/32; 435/291; 204/195 B
[58] Field of Search ................ 195/103.5 K, 103.5 R, 195/103.5 M; 435/32

[56] References Cited

U.S. PATENT DOCUMENTS

| | | | |
|---|---|---|---|
| 3,403,081 | 9/1968 | Rohrback et al. | 195/103.5 M X |
| 3,479,255 | 11/1969 | Arthur | 195/103.5 R X |
| 3,743,581 | 7/1973 | Cady et al. | 195/103.5 M X |

Primary Examiner—Raymond N. Jones
Assistant Examiner—Robert J. Warden
Attorney, Agent, or Firm—Toren, McGeady and Stanger

[57] ABSTRACT

The changes in the redox potentials of cultures of a microorganism with and without a tested growth inhibiting agent are monitored during the phase of growth in which the redox potential is normally positive and the rate of potential change is approximately linear. Effective growth inhibiting agents produce a measurable decrease in the change of the redox potential to a more negative value within less than one hour. A sensible signal indicative of the growth inhibiting action of the tested agent may be obtained from a comparator by storing an amplified signal indicative of the redox potential at a first time and feeding the stored signal together with another amplified signal obtained less than one hour thereafter to the comparator.

4 Claims, 3 Drawing Figures

METHOD OF TESTING THE EFFECTIVENESS OF A GROWTH INHIBITING AGENT ON A MICROORGANISM

This invention relates to the testing of the effectiveness of growth inhibiting agents on microorganisms, and particularly to a method of testing such effectiveness and to apparatus for performing the method.

It is common clinical practice to test in vitro the effectiveness of growth inhibiting antibiotics on unidentified microorganisms recovered from a patient before prescribing antibiotics against an infectious disease. Small, porous paper discs impregnated with small amounts of respective antibiotics are staple articles of commerce. When a culture is prepared from a specimen obtained from the patient, and the discs are introduced into the culture, the most effective antibiotic agent is readily recognized by the absence of microbial growth in the adjacent portion of the culture medium. The known method is effective, but time consuming.

The susceptibility of microorganisms to growth inhibiting factors has been determined more quickly by measuring the change in the electrical conductivity of nutrient media in which the microorganisms are grown with and without growth inhibiting materials (Cady et al., U.S. Pat. No. 3,743,581).

It has now been found that the redox potential change of the culture medium on which a tested microorganism is grown provides a very much faster indication of the effectiveness of a growth inhibiting agent in the medium, and that parallel tests performed with and without the tested growth inhibiting agent avoid the need for precise standardization of test conditions.

It has been known for almost one hundred years that microorganisms, and particularly bacteria, have a reducing effect on susceptible components of the culture medium on which they grow, and the electrometric determination of the redox potential of growing microbial cultures has been practiced for more than fifty years (H. E. Jacob, in "Methods in Microbiology", ed. by J. R. Noris and D. W. Ribbons, vol. 2, pp. 92-123, Academic Press, New York, 1970). As measured between an inert measuring electrode of polished platinum and a non-polarizable silver/silver chloride electrode of constant potential, the redox potential of a freshly inoculated, oxygen bearing culture medium is of the order of +0.1 V, remains virtually unchanged for 1 to 4 hours, and then drops rapidly to a value of the order of −0.5 V.

I have found that the minute change of redox potential in a freshly inoculated culture medium is readily monitored by means of available electronic equipment, and that the rate of change during the initial phase, that is, while the redox potential remains positive, is sufficiently affected by the presence of antibiotic agents to indicate clinically significant differences between different growth inhibiting agents.

The redox potential of the growing culture prior to the rapid drop to negative values, varies with time in such a manner that no significant error is introduced by assuming a linear rate of change. An adequate indication of the effectiveness of a growth inhibiting agent may thus be obtained from a single reading of redox potential taken at a fixed time after inoculation. A more precise measure of effectiveness is derived from the difference of two redox potentials measured as little as a few minutes apart, all readings being taken within two hours, and preferably within one hour from inoculation or less.

Apparatus for performing the method of the invention is illustrated in the appended drawing in which.

Figure 1:
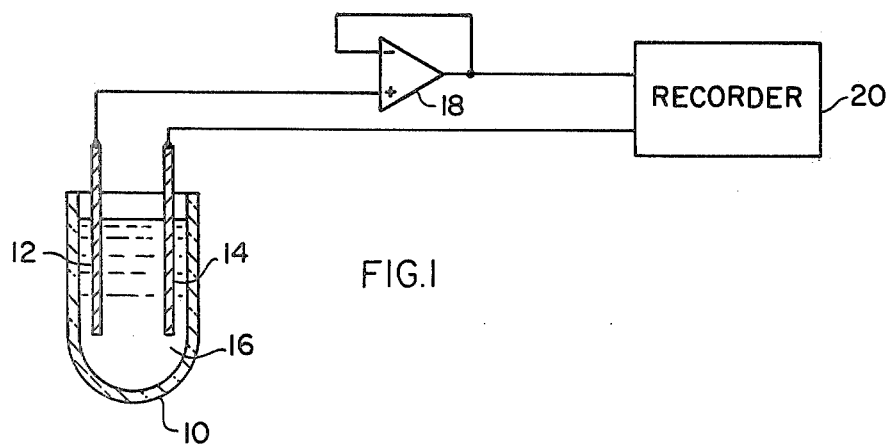
FIG. 1 shows apparatus for generating a sensible signal indicative of the redox potential of a culture medium in conventional symbols.

Referring initially to FIG. 1, there is shown a glass cell 10 in which a measuring electrode 12 of smooth platinum wire and a conventional reference electrode 14, not shown in detail, are immersed in liquid, aqueous, nutrient medium 16 inoculated with a microorganism isolate obtained from a clinical specimen. The nutrient medium is chosen to support growth of all microorganisms whose presence is suspected. The measuring electrode 12 is connected to the input of an operational amplifier 18 having an input impedance of more than $10^{10}$ ohms. The output signal of the amplifier 18 is fed to a multiple-channel recorder 20 whose stylus records the redox potential sensed by the electrode 12 as a function of time. A second cell, not illustrated, but identical with the cell 10 and identically equipped with electrodes and an amplifier, but containing a small amount of antibiotic agent on a paper disc immersed in the nutrient medium is connected to a second input of the recorder 20. The two curves simultaneously produced by the recorder 20 provide a clear indication of the growth inhibiting effectiveness of the added antibiotic agent.

In an actual run of the apparatus described above and partly illustrated in FIG. 1, the two culture cells contained each 0.5 ml sterile Trypticase broth as a culture medium. A paper disc carrying 10 mcg streptomycin was immersed in the medium in one cell. The media in the two cells were each inoculated with 20 microliters of a previously prepared culture of *Escherichia coli* in Trypticase broth, and the cells were immersed in a water bath at approximately 37° C. The amplifiers employed were operational amplifiers of commercial type 43 J employing field effect transistors, and they were connected to a recorder having a potential range of 200 mV.

30 Minutes after inoculation, the indicated redox potentials were +54.3 mV without antibiotic, +56.0 mV in the presence of streptomycin. The readings after 45 minutes were +29.2 mV and +45.4 mV respectively. Analogous differences in readings were obtained with other aerobic microorganisms, but also with anaerobic microbes when the culture media contained oxygen due to contact with air. Differences in the growth inhibiting effectiveness of different antibiotics were clearly indicated by simultaneously produced lines on the recorder chart.

Figure 2:
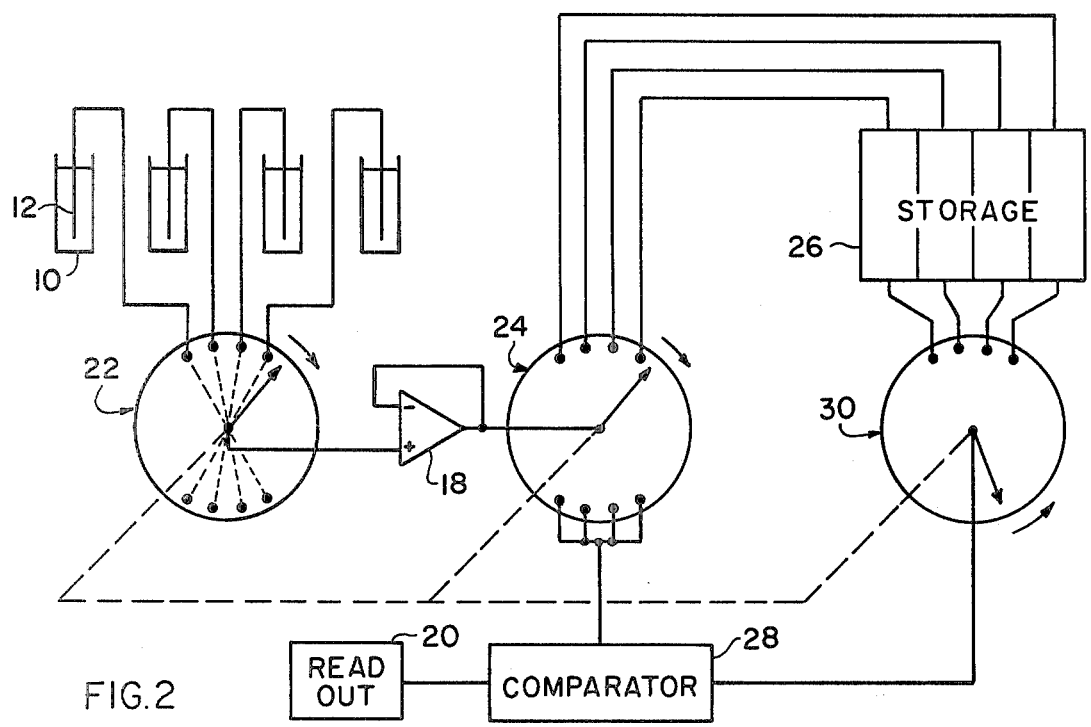
FIG. 2 is a schematic of an arrangement for automatically generating a sensible signal indicative of the difference in growth rate between cultures containing different antibiotics.

Readings indicative of microbial growth without growth inhibiting agents and in the presence of several antibiotics may be obtained by means of the apparatus shown in FIG. 2. Reference electrodes and their conventional conductive connections to other circuit elements have been omitted in order not to crowd the drawing.

The measuring electrodes 12 in four cells 10 may be connected alternatively to the input of an operational amplifier 18 by one unit 22 of an assembly of three ganged, rotatry stepping the presence of several antibiotics switches driven by a timing motor. A second unit 24 distributes the corresponding output signals of the amplifier 18 to respective sections of a memory or storage device 26. The unit 24 may also connect the output of the amplifier 18 to one input of a comparator 28 while the stepping switch 22 sequentially connects the electrodes 12 to the input of the amplifier 18, and the third stepping switch 30 sequentially connects the sections of the storage device 26 to the comparator 28. A readout 20 converts the output signals of the comparator 28 to four numbers printed on tape and respectively indicative of the microbial growths in the four cells 10.

Figure 3:
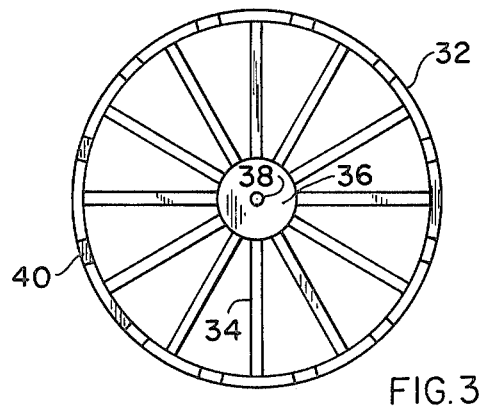
FIG. 3 is a top plan view of a partitioned cell suitable for use in the arrangement of FIG. 2.

It is usually necessary to test more than the three antibiotics capable of being handled by the cells shown in FIG. 2, and a preferred cell assembly for simultaneously testing eleven antibiotics and a control culture is shown in FIG. 3.

The cavity of a Petri dish 32 is provided with six diametrical partitions 34 sealed to the axial wall of the dish. The cylindrical space between the radially inner portions of the partitions 34 which is formed by contiguous apertures in the partitions is sealingly filled by a plug 36 of a gel prepared from physiological saline solution and agar in which a silver wire 38 coated with silver chloride is centrally embedded as a reference electrode. Films 40 of gold are deposited from the vapor phase on the circumferential walls of the compartments in the dish 32 separated by the partitions 34 as measuring electrodes.

The twelve compartments are filled with respective batches of a nutrient medium inoculated with the tested microorganism, and paper discs carrying respective growth inhibiting agents are placed in eleven of the twelve compartments. The electrodes 38, 40 are connected with an indicating arrangement differing from that shown in FIG. 2 only by the number of contacts in the ganged stepping switches 22, 24, 30. The rotary switch assembly described with reference to FIG. 2 may be replaced by its known electronic equivalent including an automatic timer circuit so that the activity of an operator may be limited to the connecting of the electrodes 38, 40 to conductors of the indicating arrangement and to the reading of the results printed by the readout.

The electrometric determination of redox potentials is a well developed art, and the apparatus described herein is merely illustrative of presently preferred practice. Many variations will readily suggest themselves to those skilled in the art on the basis of the instant teachings. It should be understood, therefore, that the above disclosure relates only to preferred embodiments of the invention, and that it is intended to cover all changes and modifications of the examples of the invention herein chosen for the purpose of the disclosure which do not constitute departures from the spirit and scope of the invention set forth in the appended claims.

What is claimed is:

1. A method of testing the effectiveness of a growth inhibiting agent on a microorganism which comprises:
    (a) introducing into a first batch of a nutrient medium an amount of the growth inhibiting agent to be tested;
    (b) introducing into said first batch and into a second batch of said nutrient medium respective inocula of said microorganism, said second batch being free of said agent and capable of supporting growth of said microorganism at a predetermined temperature;
    (c) incubating said first and second batches at said temperature;
    (d) sensing the redox potentials of the incubated batches at a predetermined time after said inoculating while said redox potentials vary at approximately linear rates; and
    (e) generating at least one sensible signal indicative of the difference between the sensed redox potentials as a measure of said effectiveness.

2. A method as set forth in claim 1, wherein said predetermined time is less than two hours.

3. A method as set forth in claim 2, wherein said predetermined time is less than one hour, said microorganism being a bacterium.

4. A method as set forth in claim 2, wherein said redox potentials are sensed while having a positive value as measured between a smooth platinum measuring electrode and a reference electrode, said nutrient medium containing dissolved oxygen.

* * * * *